US010724094B2

(12) United States Patent
Menchen et al.

(10) Patent No.: US 10,724,094 B2
(45) Date of Patent: Jul. 28, 2020

(54) CONJUGATED POLYMERIC PARTICLE AND METHOD OF MAKING SAME (71) Applicant: Life Technologies Corporation, Carlsbad, CA (US)

(72) Inventors: Steven M. Menchen, Fremont, CA (US); Alan Blanchard, Middleton, MA (US); Luisa Andruzzi, Beverly, MA (US); Shaheer H. Khan, Foster City, CA (US); Dmitriy Gremyachinskiy, San Francisco, CA (US); Alfred Lui, Sunnyvale, CA (US); Craig Stolarczyk, San Mateo, CA (US); Tanya Sokolsky, Cambridge, MA (US); Prasanna Krishnan Thwar, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 150 days.

(21) Appl. No.: 15/945,348

(22) Filed: Apr. 4, 2018

(65) Prior Publication Data

US 2018/0223359 A1 Aug. 9, 2018

Related U.S. Application Data (60) Division of application No. 14/855,705, filed on Sep. 16, 2015, now Pat. No. 9,938,577, which is a continuation of application No. 13/763,066, filed on Feb. 8, 2013, now Pat. No. 9,139,667.

(60) Provisional application No. 61/597,064, filed on Feb. 9, 2012.

(51) Int. Cl.
*C12Q 1/6876* (2018.01)
*C08F 8/40* (2006.01)
*C12Q 1/6834* (2018.01)

(52) U.S. Cl.
CPC .............. *C12Q 1/6876* (2013.01); *C08F 8/40* (2013.01); *C12Q 1/6834* (2013.01)

(58) Field of Classification Search
None
See application file for complete search history.

(56) References Cited

U.S. PATENT DOCUMENTS

| 4,451,613 | A | 5/1984 | Rousseau et al. |
| 4,507,382 | A | 3/1985 | Rousseau et al. |
| 4,507,497 | A | 3/1985 | Reilly et al. |
| 5,281,698 | A | 1/1994 | Nitecki |
| 5,387,510 | A | 2/1995 | Wu |
| 5,512,439 | A | 4/1996 | Hornes et al. |
| 5,677,373 | A | 10/1997 | Berge et al. |
| 6,242,235 | B1 | 6/2001 | Shultz et al. |
| 6,525,183 | B2 | 2/2003 | Vinayak et al. |
| 7,217,762 | B1 | 5/2007 | Joergedal et al. |
| 7,534,621 | B2 | 5/2009 | Okada |
| 9,139,667 | B2 | 9/2015 | Menchen et al. |
| 9,243,085 | B2 | 1/2016 | Fonnum et al. |
| 9,938,577 | B2 | 4/2018 | Fonnum et al. |
| 10,144,968 | B2 | 12/2018 | Fonnum et al. |
| 10,150,992 | B2 | 12/2018 | Menchen et al. |
| 2004/0014080 | A1 | 1/2004 | Tanga et al. |
| 2004/0203040 | A1 | 10/2004 | Okada |
| 2004/0215011 | A1 | 10/2004 | Deggerdal et al. |
| 2005/0014001 | A1 | 1/2005 | Fonnum et al. |
| 2006/0131542 | A1 | 6/2006 | Weng et al. |
| 2007/0299249 | A1 | 12/2007 | Songe et al. |
| 2008/0139399 | A1 | 6/2008 | Fonnum et al. |
| 2009/0026082 | A1 | 1/2009 | Rothberg et al. |
| 2009/0069554 | A1 | 3/2009 | Finne et al. |
| 2009/0081371 | A1 | 3/2009 | Minami et al. |
| 2009/0291506 | A1 | 11/2009 | Fonnum et al. |
| 2010/0137143 | A1 | 6/2010 | Rothberg et al. |
| 2010/0207051 | A1 | 8/2010 | Fonnum et al. |
| 2010/0282617 | A1 | 11/2010 | Rothberg et al. |
| 2010/0304982 | A1 | 12/2010 | Hinz et al. |
| 2013/0210991 | A1 | 8/2013 | Fonnum et al. |

FOREIGN PATENT DOCUMENTS

| EP | 0512844 | 11/1992 |
| EP | 1726661 | 11/2006 |
| EP | 2224014 | 9/2010 |
| JP | H05211899 | 8/1993 |
| JP | 2002211954 | 7/2002 |
| JP | 2004258026 | 9/2004 |
| JP | 2007003439 | 1/2007 |
| JP | 2007508416 | 4/2007 |
| JP | 2009092651 | 4/2009 |
| JP | 2009516008 | 4/2009 |
| WO | WO-2002000600 | 1/2002 |
| WO | WO-2002072791 | 9/2002 |
| WO | WO-2003084982 | 10/2003 |

(Continued)

OTHER PUBLICATIONS

Devor et al., "Strategies for Attaching Oligonucleotides to Solid Supports", Integrated DNA Technologies 2005, 2010, and 2011, US, Jan. 1, 2005, URL:https://www.idtdna.comjpagesjdocsjdefault-sourcejtechnical-reportsjstrategies-for-attaching-oligonucleotides-to v6-3-14-14.pdf?sfvrsn=2 [retrieved on Aug. 9, 2016].
Dong et al., "Effect of Secondary Structure on the Activity of Enzymes Suspended in Organic Solvents", *Archives of Biochemistry and Biophysics*, vol. 334, No. 2, Article No. 0472, 1996, 406-414.
EP17160771, Search Report, dated Sep. 14, 2017, 1-20.
EP17160771, Partial Search Report, dated Jul. 3, 2017, 1-19.
Ghosh et al., "N, N'-disuccinimidyl carbonate: a useful reagent for alkoxycarbonylation of amines", Tetrahedron Letters, vol. 33, No. 20, May 12, 1992, 2781-2784.
Haginaka et al., "Separation of enantiomers on a chiral stationary phase based on ovoglycoprotein-I. Influences of the pore size of base silica materials and bound protein amounts on chiral resolution", Journal of Chromatography A, vol. 773, Nos. 1-2, Jun. 27, 85-91.

(Continued)

*Primary Examiner* — Robert M Kelly (57) ABSTRACT

A method of conjugating a substrate includes exchanging a counter ion associated with a biomolecule with a lipophilic counter ion to form a biomolecule complex, dispersing the biomolecule complex in a nonaqueous solvent, and coupling the biomolecule complex to a substrate in the presence of the nonaqueous solvent.

17 Claims, 5 Drawing Sheets

(56) References Cited

FOREIGN PATENT DOCUMENTS

| WO | WO-2003091392 | 11/2003 |
|---|---|---|
| WO | WO-2004086046 | 10/2004 |
| WO | WO-2005017180 | 2/2005 |
| WO | WO-2005037902 | 4/2005 |
| WO | WO-2005074993 | 8/2005 |
| WO | WO-2006103094 | 10/2006 |
| WO | WO-2006125124 | 11/2006 |
| WO | WO-2007020041 | 2/2007 |
| WO | WO-2007040986 | 4/2007 |
| WO | WO-2008005675 | 1/2008 |
| WO | WO-2010125170 | 11/2010 |
| WO | WO-2011053940 | 5/2011 |
| WO | WO-2013119894 | 8/2013 |
| WO | WO-2013119936 | 8/2013 |
| WO | WO-2013119956 | 8/2013 |
| WO | WO-2017004559 | 1/2017 |
| WO | WO-2017007774 | 1/2017 |

OTHER PUBLICATIONS

Ion Torrent Systems, "GO Club (Genaris Omics Club)", http://genaport.genaris.com/GOC_sequencer_post.php?eid=00006, 2010, 1-2.

Lee, "Solubility of Tetrabutylammonium Bromide in Benzene between 298.15 K and 323.15 K", *Journal of Chemical & Engineering Data*, vol. 47, No. 5, 2002, 1135-1139.

Li et al., "Enzyme-linked synthetic oligonucleotide probes: non-radioactive detection of enterotoxigenic *Escherichia coli* in faecal specimens", *Nucleic Acids Research*, vol. 15, No. 13, Jul. 10, 1987, 5275-5287.

Ling et al., "Polymer-bound cellulose phenylcarbamate derivatives as chiral stationary phases for enantioselective HPLC", *Journal of Separation Science*, vol. 26, 2003, 1337-1346.

Meyer et al., "Hydrophobic Ion Pairing: Altering the Solubility Properties of Biomolecules", *Pharmaceutical Research*, vol. 15, No. 2, 1998, 188-193.

Murakami et al, Hybrid Hydrogels to Which Single-Stranded (ss) DNA Probe Is Incorporated Can Recognize Specific ssDNA, 2005, *Macromolecules*, vol. 38, 2005, 1535-1537.

Nemat-Gorgani et al., "The Interaction of Phospholipid Membranes and Detergents with Glutamate Dehydrogenase", *European Journal of Biochemistry*, vol. 74, No. 1, Mar. 1977, 129-137.

Nimse et al: "Immobilization Techniques for Microarray: Challenges and Applications", *Sensors*, vol. 14, No. 12, Nov. 25, 2014, 22208-22229.

Ogura, et al., "A Novel Active Ester Synthesis Reagent", *Tetrahedron Letters*, vol. 49, Jan. 1, 1979, 4745-4746.

PCT/US2013/025352, International Preliminary Report on Patentability, dated Aug. 12, 2014, 1-11.

PCT/US2013/025352, International Search Report and Written Opinion, dated May 22, 2013, 1-18.

PCT/US2016/040767, International Preliminary Report on Patentability, dated Jan. 11, 2018, 1-9.

PCT/US2016/040767, International Search Report and Written Opinion, dated Oct. 11, 2016, 1-14.

PCT/US2016/041012, International Search Report and Written Opinion, dated Oct. 4, 2016, 2017, 1-10.

PCT/US2016/041012, International Preliminary Report on Patentability, dated Jan. 9, 2018, 1-6.

Peppas et al., "Hydrogels in Biology and Medicine: From Molecular Principles to Bionanotechnology", *Advanced Materials*, vol. 18, 2006, 1345-1360.

Poellmann et al., "Characterizing and Patterning Polyacrylamide Substrates Functionalized with N-Hydroxysuccinimide", *Cellular and Molecular Bioengineering*, vol. 6, No. 3, Sep. 2013, 299-309.

Powers et al., "Enhanced Solubility of Proteins and Peptides in Nonpolar Solvents Through Hydrophobic Ion Pairing", *Biopolymers*, vol. 33, No. 6, 1993, 927-932.

Tang et al., "Polymerizing immobilization of acrylamide-modified nucleic acids and its application", *Biosensors and Bioelectronics*, vol. 24, No. 7, Mar. 15, 2009, 1817-1824.

Wang et al., "Different EDC/NHS activation mechanisms between PAA and PMAA brushes and the following amidation reactions", *Langmuir: The Acs Journal of Surfaces and Colloids*, vol. 27, No. 19, Oct. 4, 2011, 12058-12068.

Wilchek et al., "improved method for preparing n-hydroxysuccinimide ester-containing polymers for affinity chromatography", *Bioconjugate Chemistry*, vol. 5, No. 5, Jan. 1, 1994, 491-492.

Xion et al, "Responsive ONA-Based Hydrogels and Their Applications", *Macromolecular Rapid Communications*, vol. 34, No. 16, Jul. 16, 2013, 1271-1283.

CONJUGATED POLYMERIC PARTICLE AND METHOD OF MAKING SAME

CROSS-REFERENCE TO RELATED APPLICATION(S)

This application is a divisional application under 35 U.S.C. § 120 of pending U.S. application Ser. No. 14/855,705 filed Sep. 16, 2015, which is a continuation of U.S. application Ser. No. 13/763,066 filed Feb. 8, 2013 (now U.S. Pat. No. 9,139,667), which application claims the benefit under 35 U.S.C. § 119(e) of U.S. Provisional Application No. 61/597,064 filed Feb. 9, 2012. The entire contents of the aforementioned applications are incorporated by reference herein.

FIELD OF THE DISCLOSURE

This disclosure, in general, relates to methods of conjugating a substrate and substrates formed through such methods.

BACKGROUND

The conjugation of polynucleotides to substrates has become of interest to various industries. Substrates including conjugated polynucleotides are useful in separation techniques, detection of genetic markers, and sequencing.

For example, a substrate conjugated with a polynucleotide probe can be used for capturing genetic markers for detection. Exemplary genetic markers can be related to disease variants within a gene, disease causing bacteria or viruses, or alleles useful in human identification. Substrates including conjugated probes complementary to a genetic marker can capture such a genetic marker, and various techniques can be used to detect the presence of the captured genetic marker.

In another example, a substrate conjugated with a polynucleotide can be useful in capturing and separating genetic material. In an example, probes on a substrate can be complementary to a desired polynucleotide. The probes can be configured to capture the desired polynucleotide and later release the polynucleotide to permit recovery of the polynucleotide. In another example, polymeric particles conjugated with polynucleotide probes that are complementary to target polynucleotides can be used to capture and separate a target polynucleotide from solution. Subsequently, the target polynucleotide can be released from the conjugated particle in a different solution.

In a further example, a substrate conjugated to a polynucleotide can be used in various sequencing techniques. For example, a polymeric particle conjugated to a polynucleotide or multiple copies of the polynucleotide can be used in sequencing techniques, such as fluorescent-based sequencing techniques or ion-based sequencing techniques.

While each of the above uses of conjugated substrates is of particular interest to various industries, reliable conjugation of a polynucleotide to a substrate, such as a polymeric substrate, is often inefficient. Such inefficiencies lead to lower densities of the conjugated polynucleotide or random regions devoid of the desired polynucleotide. Such inefficiencies can result in poor separations, low accuracy in detection methods, and low signal or high signal-to-noise ratio in sequencing techniques.

As such, an improved conjugation method would be desirable.

SUMMARY

In a first aspect, a method of conjugating a substrate includes exchanging a counter ion associated with a biomolecule with a lipophilic counter ion to form a biomolecule complex, dispersing the biomolecule complex in a nonaqueous solvent, and coupling the biomolecule complex to a substrate in the presence of the nonaqueous solvent.

In a second aspect, a method of conjugating a polymeric particle includes exchanging a cationic counter ion associated with a polynucleotide with a lipophilic cationic counter ion to form a polynucleotide complex, the polynucleotide including a nucleophilic or an electrophilic reactive group. The method further includes dispersing the polynucleotide complex in a non-reactive, nonaqueous solvent and coupling the polynucleotide to the polymeric particle by nucleophilic or electrophilic substitution, the polymeric particle including an electrophilic group or a nucleophilic group.

In a third aspect, a polymeric particle includes a polymer conjugated to a polynucleotide using the method of any one of above aspects or examples.

In a fourth aspect, a method of sequencing includes amplifying a target polynucleotide in the presence of an oligonucleotide conjugated polymeric particle to form the polynucleotide conjugated polymeric particle. The oligonucleotide is at least partially complementary to the target polynucleotide. The oligonucleotide conjugated polymeric particle is formed by the method of any of the above aspects or examples. The method further includes applying the polynucleotide conjugated polymeric particle to a sequencing device, applying a primer to the polynucleotide conjugated polymeric particle, incorporating a nucleotide, and detecting the incorporating.

In a fifth aspect, a method of isolating a target polynucleotide includes contacting a first solution including the target polynucleotide with a probe conjugated substrate. The probe of the probe conjugated substrate is at least partially complementary to the target polynucleotide. The probe conjugated substrate is formed by the method of any of the above aspects or examples. The method further includes washing the probe conjugated substrate while the target polynucleotide is coupled to the probe and releasing the target polynucleotide in a second solution.

In an additional aspect, a method of conjugating an oligonucleotide to a polymer includes treating a polymer comprising amine functionality with a bis-NHS ester or a disuccinimidyl carbonate to form a functionalized polymer and treating the functionalized polymer with an amine terminated oligonucleotide to form a conjugated polymer including the oligonucleotide.

BRIEF DESCRIPTION OF THE DRAWINGS

The present disclosure may be better understood, and its numerous features and advantages made apparent to those skilled in the art by referencing the accompanying drawings.

DETAILED DESCRIPTION

In an embodiment, a method of conjugation includes exchanging counter ions associated with a biomolecule with lipophilic counter ions to form a biomolecule complex. In an example the counter ions are cationic. The biomolecule complex, such as a polynucleotide complex, can be dispersed in a nonaqueous solvent and conjugated to a substrate in the presence of the nonaqueous solvent. An exemplary substrate includes a surface, such as a ceramic, metallic, or polymeric surface. In another example, a substrate includes a swellable polymeric particle. In particular, the biomolecule can be conjugated to functional groups of the swellable polymer throughout the polymeric particle.

In example, the conjugated substrate can be used to capture a target polynucleotide. In a particular example, the conjugated polynucleotide can be extended based on the captured target polynucleotide. In the case of a polymeric particle including multiple copies of the conjugated polynucleotide, copies of the conjugated polynucleotide can be extended in accordance with a target polynucleotide to provide multiple copies of a complement to the target polynucleotide. Such a particle can be useful in sequencing techniques, such as ion or pH-based sequencing techniques.

In particular, the present method performs conjugation within a nonaqueous solution. It has been discovered that water can compete with or interfere with various conjugation chemistries, reducing conjugation efficiency. For example, water can interfere with nucleophilic or electrophilic substitution. Water can compete with the nucleophile for the electrophile by hydrolyzing the electrophile to an inactive moiety for conjugation. By conjugating in a nonaqueous solution or solvent, conjugation methods, such as nucleophilic or electrophilic substitution, become more efficient. In addition, new conjugation chemistries can be utilized in a nonaqueous environment.

A biomolecule can include nucleosides, nucleotides, nucleic acids (oligonucleotides and polynucleotides), polypeptides, saccharides, polysaccharides, lipids, and derivatives or analogs thereof. In a particular example, the biomolecule is a polypeptide or a nucleic acid, such as a polynucleotide. For example, the biomolecule can be a polynucleotide or an analog thereof.

Figure 1:
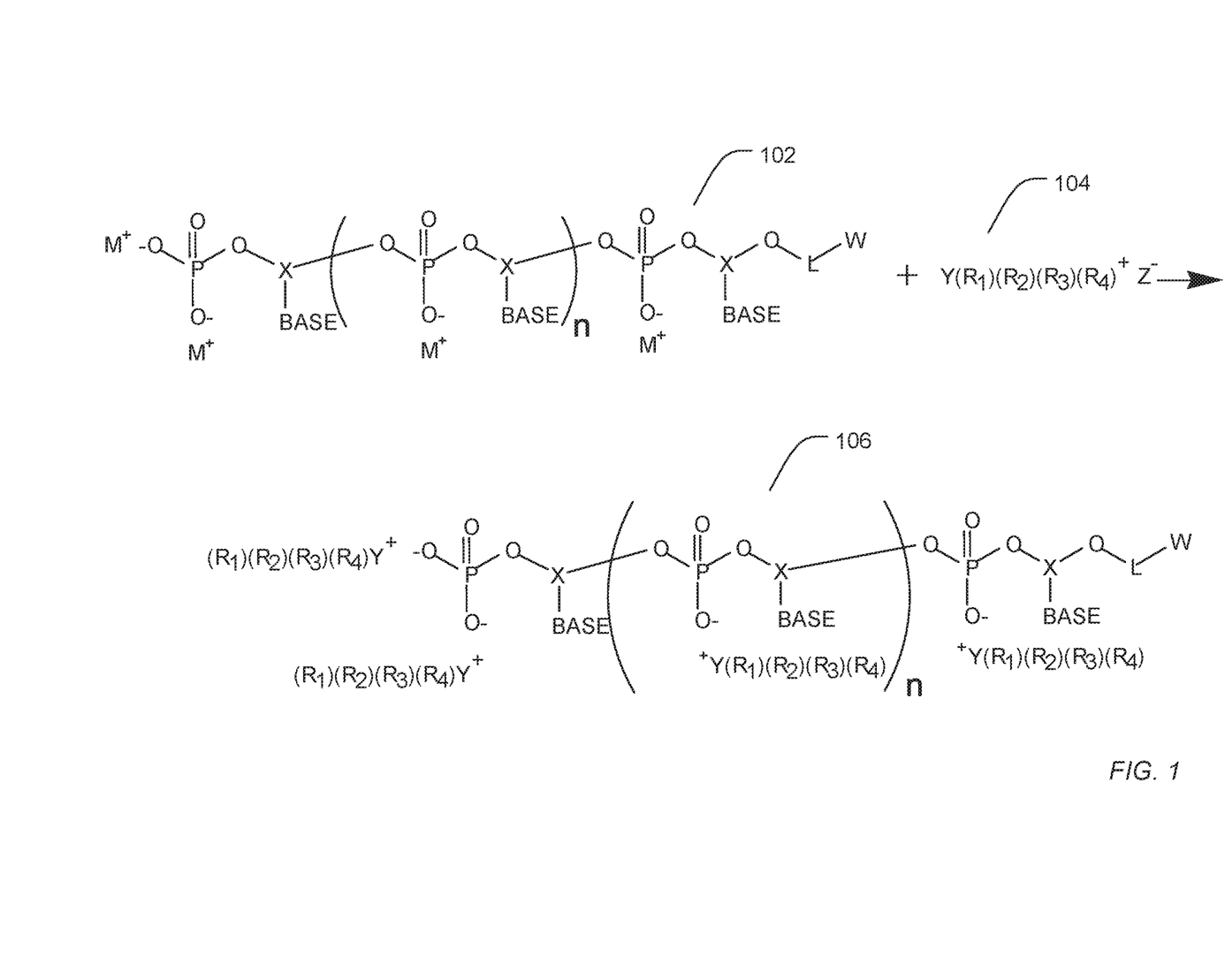
FIG. 1 includes an illustration of an exemplary method for treating polynucleotides.

As illustrated in FIG. 1, counter ions of a biomolecule can be exchanged with lipophilic counter ions to provide a biomolecule complex that is more lipophilic. The illustrated biomolecule is a polynucleotide 102. As illustrated, the polynucleotide 102 is formed of a plurality of polymerized nucleotides. The carbohydrate moiety (X) of a nucleotide is bound to a phosphate group of a neighboring nucleotide. Each phosphate group is associated with a cationic counter ion (M). In an example, the cationic counter ion (M) can be a metal ion. In another example, the cationic counter ion (M) can be ammonium or proton. In addition, the polynucleotide 102 can include a linker group (L), linking a reactive group (P) to the nucleotide chain. Alternatively, the biomolecule can be a polynucleotide analog having a similar linker/reactive group structure, and the polynucleotide can have the reactive group (P) extending off one or more of the bases in addition to or instead of off the carbohydrate (X).

In an example, the linker group (L) includes a hydrocarbon, an ether or polyether group, or a combination thereof. The reactive group (P) can function to react with functional groups formed on a substrate, such as a polymeric substrate. In a particular example, the reactive group (P) can be an amine, thiol, maleimide, acetylene, azide, or a combination thereof. For example, the reactive group (P) can be an amine or a thiol. In particular, the reactive group (P) can be an amine. In an example, the reactive group (P) can be a maleimide. In a further example, the reactive group (P) can be acetylene. In a further example, the reactive group (P) can be an azide.

The polynucleotide 102 is exposed to a lipophilic counter ion 104. The lipophilic counter ion 104 can include a positively charged member (Y) coupled to one or more hydrocarbon groups (R1, R2, R3, R4) and associated with an opposing ion (Z). In an example, the positively charged member (Y) can be nitrogen, phosphorus, sulfur, arsenic, or any combination thereof. In particular, the positively charged member (Y) is nitrogen, phosphorous, sulfur, or a combination thereof. For example, the positively charged member (Y) can be a nitrogen or phosphorous. In particular, the positively charged member (Y) is nitrogen, forming an amine with hydrocarbon groups (R1, R2, R3, or R4).

The positively charged member (Y) includes one or more hydrocarbon groups, such as at least two hydrocarbon groups, at least three hydrocarbon groups, or at least four hydrocarbon groups. As illustrated, the positively charged member (Y) includes four hydrocarbon groups (R1, R2, R3, or R4). The hydrocarbon groups (R1, R2, R3, or R4) independently can be an alkyl group, an aryl group, ether derivatives thereof, or combinations thereof. In an example, an alkyl hydrocarbon group can include a methyl, ethyl, propyl, or butyl group, an ether derivative thereof, or a combination thereof. For example, the propyl can be an n-propyl, an iso-propyl, or a combination thereof. In an example, the butyl group can be an n-butyl, isobutyl, sec-butyl, tert-butyl, or any combination thereof. An exemplary aryl group can include a phenyl, tolyl, xylyl, or poly-aryl, such as naphthyl, ether derivatives thereof, or any combination thereof.

In particular, the lipophilic group [Y(R1)(R2)(R3)(R4)] can include a lipophilic ammonium ion, a lipophilic phosphonium ion, a lipophilic arsonium ion, a lipophilic sulfonium ion, or a combination thereof. An exemplary lipophilic ammonium ion includes a tetraalkylammonium, a tetraarylammonium, mixed alkyl and aryl ammonium, or a combination thereof. For example, an exemplary lipophilic ammonium ion is selected from the group consisting of tetramethylamonium, tetraethylamonium, tetrapropylamonium, tetrabutylamonium, tetrapentylamonium, tetrahexylamonium, tetraheptylamonium, tetraoctylamonium, alkyl and aryl mixtures thereof, and a combination thereof. An exemplary lipophilic phosphonium ion includes tetraphenylphosphonium. An exemplary lipophilic arsonium ion is a tetraalkylarsonium, a tetraarylarsonium, a mixed alkyl and aryl arsonium ion, or a combination thereof. For example, the lipophilic arsonium ion is tetraphenylarsonium. An exemplary lipophilic sulfonium ion is a trialkylsulfonium ion. The ion (Z) can be an ion of opposite charge to the lipophilic group [Y(R1)(R2)(R3)(R4)], such as a hydroxide, a halogen, a nitrate, a carbonate, a sulfate, a perchlorate, a phenolate, a tetraalkylborate, a tetraarylborate, a phosphate ion, or any combination thereof.

As a result of the exchange, the polynucleotide complex 106 exhibits lipophilic behavior and can be dispersed in a nonaqueous solvent. In an example, the nonaqueous solvent is polar. In a further example, the nonaqueous solvent is not reactive with coupling groups on the substrate or functional groups of the polymer, such as the reactive group (P) of the polynucleotide complex 106. In an example, the solvent includes an amide, a urea, a carbonate, an ether, a sulfoxide, a sulfone, a hindered alcohol, or a combination thereof. An exemplary amide or urea includes formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, or a combination thereof. An exemplary carbonate includes dimethyl carbonate, propylene carbonate, or a combination thereof. An exemplary ether includes tetrahydrofuran. An exemplary sulfoxide or sulfone includes dimethylsulfoxide, dimethylsulfone, or a combination thereof. An exemplary hindered alcohol includes tert-butyl alcohol.

Following the exchange or as part of the exchange, the polynucleotide complex 106 can be dispersed in the non-aqueous solvent. The dispersed polynucleotide complex 106 can be used in conjugation of a substrate.

The substrate can be a solid surface, a particle, or a combination thereof. In an example, the substrate can be a solid surface. The substrate can include planar, concave, or convex surfaces, or any combination thereof. A substrate can comprise texture or features, including etching, cavitation or bumps. Alternatively, the substrate can lack any texture or features. The substrate can include capillary structures, channels, grooves, wells or reservoirs. In an example, the substrate can be a mesh. The substrate can be porous, semi-porous or non-porous. In a further example, the substrate can be a filter or gel. The substrate can include the top of a pin (e.g., pin arrays). The substrate may be made from materials such as glass, borosilicate glass, silica, quartz, fused quartz, mica, polyacrylamide and N-substituted polyacrylamides, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond). In particular, the substrate can include a solid substrate having a metal film or metal coating.

In a particular example, a substrate includes polymeric particles having porosity that permits the diffusion of the polynucleotide complex 106 within the polymeric particle. In particular, the polymeric particle can include reactive functional groups that are reactive to the reactive group (P) of the polynucleotide complex 106. In an example, the polymeric particles are hydrophilic. The polymeric particle can be swellable. For example, the polymeric particle can be a hydrogel. The hydrophilic polymeric particle can expose functional groups, such as hydroxyl groups or amine groups. Such groups can be replaced with other functional groups to facilitate conjugation with the polynucleotide complex 106.

In an example, the polymeric particle can be formed of styrenic polymers, acrylate polymers, acrylamide polymers, or a combination thereof. For example, the polymeric particle can be formed from polymerized monomers. The monomer can be a radically polymerizable monomer, such as a vinyl-based monomer. In particular, the monomer can include a hydrophilic monomer. In an example, the hydrophilic monomer can include acrylamide, vinyl acetate, hydroxyalkylmethacrylate, or any combination thereof. In a particular example, the hydrophilic monomer is an acrylamide, such as an acrylamide including hydroxyl groups, amino groups, or a combination thereof. In an example, the hydrophilic monomer is an aminoalkyl acrylamide. In another example, the acrylamide can be a hydroxyalkyl acrylamide, such as hydroxyethyl acrylamide. In particular, the hydroxyalkyl acrylamide can include N-[tris(hydroxymethyl)methyl]acrylamide, N-(hydroxymethyl)acrylamide, or a combination thereof. In a particular example, the monomer includes hydroxyl groups. In a further example, a comonomer can be included, such as an aminoacrylamide, for example, an acrylamide functionalized with an amine terminated polyethylene glycol or acrylopiperazine.

In an example, the polymer of the polymeric particle can be formed from polymerizing a monomer and a crosslinker. In an example, the crosslinker is included in a mass ratio of monomer to crosslinker in a range of 15:1 to 1:2, such as a range of 10:1 to 1:1, a range of 6:1 to 1:1, or even a range of 4:1 to 1:1. In particular, the crosslinker can be a divinyl crosslinker. For example, a divinyl crosslinker can include a diacrylamide, such as N,N'-(ethane-1,2-diyl)bis(2-hydroxyethyl)acrylamide, N,N'-(2-hydroxypropane-1,3-diyl)diacrylamide, or a combination thereof. In another example, a divinyl crosslinker includes ethyleneglycol dimethacrylate, divinylbenzene, hexamethylene bisacrylamide, trimethylolpropane trimethacrylate, ethylene dimethacrylate, or a combination thereof.

In an example, the polymeric particle can be a hydrophilic particle, such as a hydrogel particle. A hydrogel is a polymer that can absorb at least 20% of its weight in water, such as at least 45%, at least 65%, at least 85%, at least 100%, at least 300%, at least 1000%, at least 1500% or even at least 2000% of its weight in water.

The polymeric particles can have a desirable particle size, such as a particle size not greater than 100 μm, not greater than 30 μm, or not greater than 3 μm. The average particle size is the mean particle diameter. For example, the average particle size may be not greater than 2 μm, such as not greater than 1.5 μm, not greater than 1.1 μm, not greater than 0.8 μm, not greater than 0.6 μm, not greater than 0.5 μm, or even not greater than 0.3 μm. In a particular example, the average particle size can be in a range of 0.1 μm to 100 μm, such as a range of 0.1 μm to 50 μm or a range of 0.1 μm to 1.1 μm.

In a further example, the plurality of particles is monodisperse and may have a desirably low coefficient of variance, such as a coefficient of variance of not greater than 20%. The coefficient of variance (CV) is defined as 100 times the standard deviation divided by average, where "average" is the mean particle diameter and standard deviation is the standard deviation in particle size. The "average" alternatively can be either the z-average or mode particle diameter. In accordance with usual practice, CV is calculated on the main mode, i.e., the main peak, thereby excluding minor peaks relating to aggregates. Thus, some particles below or above mode size may be discounted in the calculation which may, for example, be based on about 90% of total particle number of detectable particles. Such a determination of CV is performable on a CPS disc centrifuge or a coulter counter. For example, the coefficient of variance (CV) of the polymeric particles may be not greater than 15%, such as not greater than 10%, not greater than 5%, not greater than 4.5%, not greater than 4.0%, not greater than 3.5%, or even not greater than 3.0%.

In a further example, a hydrophilic polymeric particle in water can be not greater than 50 wt % polymer, such as not greater than 30 wt % polymer, not greater than 20 wt % polymer, not greater than 10 wt % polymer, not greater than 5 wt % polymer, or even not greater than 2 wt % polymer.

In an additional example, the polymeric particle can have a porosity permitting diffusion of polynucleotides, proteins or enzymes. In an example, the polymeric particles can have a porosity to permit diffusion of proteins having a size of at least 50 kilodaltons, such as at least 100 kilodaltons, at least 200 kilodaltons, at least 250 kilodaltons, or even at least 350 kilodaltons.

Whether a solid surface or a polymeric particle, such as the polymeric particles described above, the polynucleotide complex 106 illustrated in FIG. 1 can be conjugated to a substrate in the presence of a nonaqueous solvent. For example, a polymer of a substrate can include hydroxyl groups. A portion of the hydroxyl groups can be replaced with alternative functional groups to facilitate conjugation with a polynucleotide complex, such as the polynucleotide complex 106 illustrated in FIG. 1.

A substrate can undergo direct conjugation or indirect conjugation. In a particular example, the functional groups of the polymer, such as a hydroxyl group, can undergo nucleophilic or electrophilic substitution to conjugate the polymer to a polynucleotide. For example, the coupling group of a substrate can include one of a nucleophile or an electrophile and the terminal reactive group of the polynucleotide can include the other of the nucleophile or the electrophile. The polynucleotide can be coupled to the polymeric particle by nucleophilic or electrophilic substitution. In an example, direct conjugation of a polymer including a hydroxyl group can include replacing the hydroxyl group with a sulfonate ester that is subsequently conjugated to a oligonucleotide or polynucleotide including an amine or a thiol reactive group. For example, hydroxyl groups on a polymeric particle can be activated by replacing at least a portion of the hydroxyl groups with a sulfonate ester group. Exemplary sulfonate ester groups can be derived from tresyl, mesyl, tosyl, or fosyl chloride, or any combination thereof, to provide the sulfonate ester functional group in place of at least a portion of the hydroxyl groups. Sulfonate esters can act to permit nucleophiles to replace the sulfonate ester. The sulfonate ester may further react with liberated chlorine to provide chlorinated groups that can be used in a process to conjugate the particles. Alternatively, hydroxyl groups can be replaced with halogen groups which are reactive with the reactive groups of a polynucleotide complex. In a further example, amine groups of comonomers of the polymeric polymer can be reactive with reactive groups of the polynucleotide complex.

Figure 2:
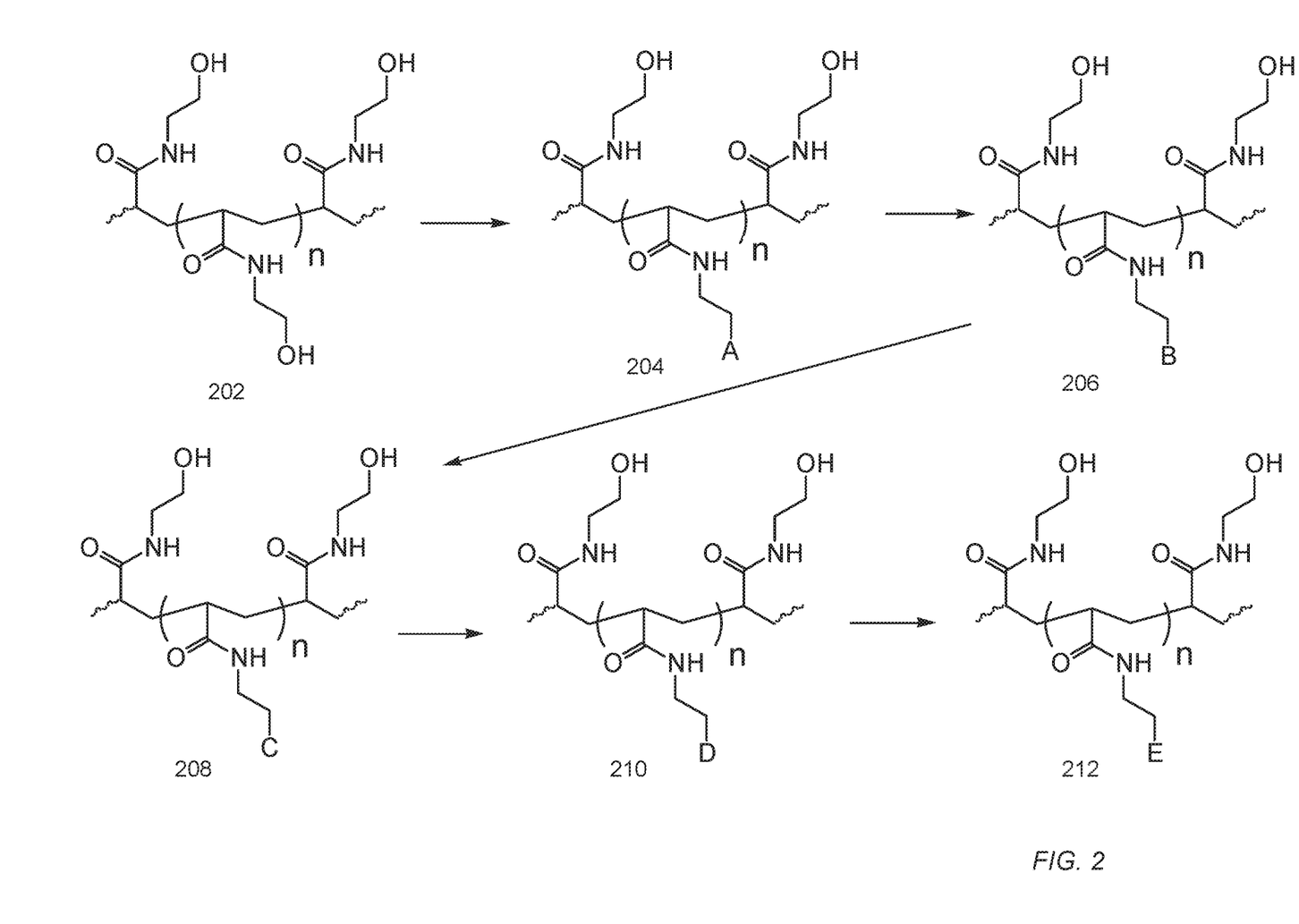
FIG. 2 includes an illustration of an exemplary conjugation method.

Alternatively, the conjugation may be indirect in which polymer functional groups, such as hydroxyl groups, are replaced through a series of substitutions, resulting in a functional group (coupling group) that can be reacted with a reactive group of a polynucleotide complex. For example, FIG. 2 illustrates a polymer 202 that includes hydroxyl groups, which can be substituted with functional groups through a series of one or more substitutions.

For example, at 204, at least a portion of the hydroxyl groups can be replaced with a functional group (A), such as a sulfonate ester, a halogen other than fluorine, or a combination thereof. Such functional groups (A) can further be replaced, as illustrated at 206, with a functional group (B), such as an azide, phthalimide, thioester, N-protected diamine, N-protected aminothioether, amino(oligonuceotide), or a combination thereof. Optionally, such functional groups (B) can be further activated, as illustrated at 208, with a functional group (C), such as an amine, thiol, or combination thereof. Moreover, such functional groups (C), illustrated at 208, can be replaced with functional groups (D), as illustrated at 210, such as monoamide-mono(NHS ester) dicarboxylic acid, succinimide thioether (oligonucleotide), or a combination thereof. Even further, the functional group (D) illustrated at 210 can be replaced, as illustrated at 212, with a functional group (E), such as a monoamide-(amino-oligonucleotide)-monoamide dicarboxylic acid. As such, the functional groups of the original polymer can undergo one or more of a series of substitutions providing reaction sites suitable for reacting with a polynucleotide complex.

Alternatively, an acrylamide polymer having amine functionality can be used in place of the polymer including hydroxyl groups. For example, the illustrated hydroxyl groups can be replaced with an amine terminated polyether (e.g., amine terminated PEG) group. With amine functionality, the illustrated method can begin, for example, at (C).

In a particular example, the functional group (A) at 204 can be a sulfonate ester, a halogen, or a combination thereof. In particular, the halogen is a halogen other than fluorine, such as chlorine. The functional group (A) can react with the polynucleotide complex 106 where the linker group (L) is a hydrocarbon or polyether and the reactive group (P) is an amine in a non-aqueous solvent to yield functional group (B) at 206, such as an amino(oligonucleotide). In another example in which the functional group (A) at 204 is replaced by functional group (B) at 206, the functional group (A) can be a sulfonate ester, halogen, or a combination thereof, and the functional group (B) can be in an azide, phthalimide, mono(N-protected)-diamine, or N-protected aminothioether. The functional group (B) can be further activated to a functional group (C), such as an amine. The amine functional group (C) can be further activated with a functional group (D), such as a (mono-amide)-(mono-NHS ester) dicarboxylic acid. The functional group (D) can be further substituted with functional group (E), such as an (amino (oligonucleotide))-dicarboxylic acid by reacting with the polynucleotide complex 106 that includes a linking group (L) of hydrocarbon or polyether and a reactive functional group (P) of an amine, in a non-aqueous solvent. Alternatively, the polymer particle can be a copolymer including a comonomer that includes amine functional groups. Such amine functional groups can be reactive with In a further example, the functional group (A) is a sulfonate ester, a halogen, or combination thereof. The functional group (B) is an azide. In such a case, the functional group (B) can be substituted with a functional group (C), such as an (oligonucleotide)triazole. The polynucleotide complex includes a linker group (L) of a hydrocarbon or polyether and a reactive functional group (P) of acetylene.

In an additional example, the functional group (A) can be a sulfonate ester, halogen, or a combination thereof. The functional group (A) is substituted with a functional group (B), such as a thioester. The thioester functional group (B) can be substituted with a functional group (C), such as a thiol, which is further substituted by the functional group (D), such as a succinimide thioether (oligonucleotide). In such an example, the polynucleotide complex can include a linker (L), such as a hydrocarbon or polyether, and a reactive group (P), such as a maleimide.

Other activation chemistries include incorporating multiple steps to convert a specified functional group to accommodate specific desired linkages. For example, the sulfonate modified hydroxyl group can be converted into a nucleophilic group through several methods. In an example, reaction of the sulfonate ester with azide anion yields an azide substituted hydrophilic polymer. The azide can be used directly to conjugate to an acetylene substituted biomolecule via "CLICK" chemistry that can be performed with or without copper catalysis. Optionally, the azide can be converted to amine by, for example, catalytic reduction with hydrogen or reduction with an organic phosphine. The resulting amine can then be converted to an electrophilic group with a variety of reagents, such as di-isocyanates, bis-NHS esters, cyanuric chloride, or a combination thereof. In an example, using di-isocyanates yields a urea linkage between the polymer and a linker that results in a residual isocyanate group that is capable of reacting with an amino substituted biomolecule to yield a urea linkage between the linker and the biomolecule. In another example, using bis-NHS esters yields an amide linkage between the polymer and the linker and a residual NHS ester group that is capable of reacting with an amino substituted biomolecule to yield an amide linkage between the linker and the biomolecule. An exemplary bis-NHS ester includes bis-succinimidyl C2-C12 alkyl esters, such as bis-succinimidyl suberate or bis-succinimidyl glutarate. In a further example, using cyanuric chloride yields an amino-triazine linkage between the polymer and the linker and two residual chloro-triazine groups one of which is capable of reacting with an amino substituted biomolecule to yield an amino-triazine linkage between the linker and the biomolecule. Other nucleophilic groups can be incorporated into the particle via sulfonate activation. For example, reaction of sulfonated particles with thiobenzoic acid anion and hydrolysis of the consequent thiobenzoate incorporates a thiol into the particle which can be subsequently reacted with a maleimide substituted biomolecule to yield a thio-succinimide linkage to the biomolecule. Thiol can also be reacted with a bromo-acetyl group.

In a further example, a polymer particle can be treated to form amine functionality that can be conjugated through the use a bis-NHS ester or a disuccinimidyl carbonate. An exemplary bis-NHS ester includes bis-succinimidyl C2-C12 alkyl esters, such as bis-succinimidyl suberate or bis-succinimidyl glutarate. For example, a polymeric particle, such as a particle including exposed hydroxyl groups, can be treated to replace the hydroxyl groups with a halogen, such as chlorine. The particle can be further treated under acid conditions with a tBOC (N-tert-butoxycarbonyl) protected amine terminated polyether, such as polyethylene glycol (PEG), providing amine functionality that can be further used to conjugate the polymer particle. Alternatively, the polymer particle can be polymerized using monomers that provide the amine functionality. The polymer particle including the amine group can be further treated using a bis-NHS ester or a disuccinimidyl carbonate, which is further exposed to an amine terminated oligonucleotide, resulting a polymer particle conjugated to the oligonucleotide.

Following conjugation, the polymeric particle can include a density of polynucleotides, termed nucleotide density, of at least $7\times10^4$ per $\mu m^3$. For example, the nucleotide density can be at least $10^5$ per $\mu m^3$, such as at least $10^6$ per $\mu m^3$, at least $2\times10^6$ per $\mu m^3$, at least $5\times10^6$ per $\mu m^3$, at least $8\times10^6$ per $\mu m^3$, at least $1\times10^7$ per $\mu m^3$, or even at least $3\times10^7$ per $\mu m^3$.

Figure 3:
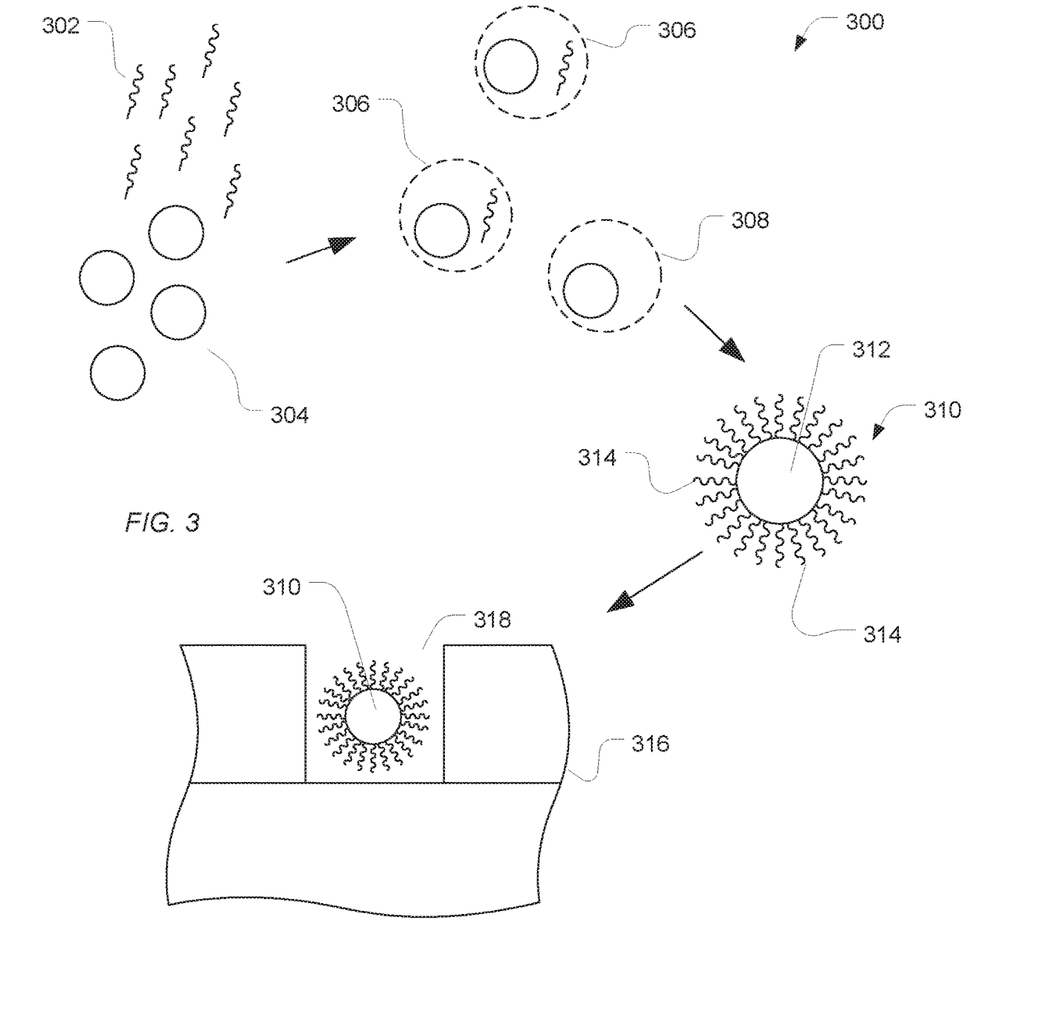
FIG. 3 includes an illustration of an exemplary sequencing method.

In a particular example, the conjugated particles can be used in separation techniques or sequencing techniques. For example, the conjugated particles can be used to capture target polynucleotides. In an example, the polynucleotides conjugated to the polymer can be extended based on captured target polynucleotides. Such conjugated particles can be use in sequencing techniques, such as a ion-based or pH-based sequencing techniques. As illustrated in FIG. 3, a plurality of conjugated polymeric particles 304 can be placed in a solution along with a plurality of target polynucleotides 302. The plurality of particles 304 can be conjugated with probe polynucleotides to bind with target polynucleotides 302. For example, the conjugated particles 304 can include an oligonucleotide complementary to a portion of the target polynucleotides 302.

In a particular embodiment, the particles 304 and polynucleotides 302 are subjected to polymerase chain reaction (PCR) amplification. For example, dispersed phase droplets 306 or 308 are formed as part of an emulsion and can include a hydrophilic particle or a polynucleotide. In an example, the target polynucleotides 302 and the hydrophilic particles 304 are provided in low concentrations and ratios relative to each other such that a single polynucleotide 302 is likely to reside within the same dispersed phase droplets as a single hydrophilic particle 304. Other droplets, such as a droplet 308, can include a single hydrophilic particle and no polynucleotide. Each droplet 306 or 308 can include enzymes, nucleotides, salts or other components sufficient to facilitate duplication of the polynucleotide.

Duplication of the target polynucleotide can include modulating the duplication conditions. Modulating can optionally include: increasing or decreasing the polymerase concentration; increasing or decreasing the nucleotide concentration; increasing or decreasing a cation concentration; increasing or decreasing a reaction temperature, time or pH, and the like. Modulating can include increasing or decreasing the rate of the reaction, increasing or decreasing the yield of product of the reaction, and the like. Duplication can be performed in the presence of appropriate buffers or nucleotides (including nucleotide analogs or biotinylated nucleotides).

In particular, the polynucleotide to be amplified can be captured by the polymeric particle. Exemplary methods for capturing nucleic acid can include: hybridizing a polynucleotide to an oligonucleotide that is attached to a polymeric particle. Methods for capturing nucleic acids can include: (a) providing a polymeric particle attached to a single-stranded oligonucleotide (e.g., a capture oligonucleotide); (b) providing a single-stranded polynucleotide; and (c) hybridizing the single-stranded oligonucleotide to the single-stranded polynucleotides, thereby capturing the single-stranded polynucleotide to the polymeric particle. Each of the polymeric particles can be attached with a plurality of single-stranded oligonucleotides (e.g., capture oligonucleotides). In some embodiments, step (c) can be conducted with a plurality of single-stranded polynucleotides. In some embodiments, at least a portion of the single-stranded oligonucleotide includes a nucleotide sequence that is complementary (or partially complementary) to at least a portion of the single-stranded polynucleotide.

In an example, the method can further include amplifying the polynucleotide into a plurality of polynucleotides and attaching at least a portion of the plurality of polynucleotides to the hydrophilic particle, thereby generating a hydrophilic particle including a plurality of attached polynucleotides. Alternatively, the method can include amplifying the polynucleotide into a plurality of complementary polynucleotides by extending the conjugated oligonucleotide, thereby generating a hydrogel particle including a plurality of attached polynucleotides.

In a further example, methods for nucleotide incorporation can include: conducting a nucleotide polymerization reaction on a polynucleotide that is hybridized to an oligonucleotide that is attached to a polymeric particle. In some embodiments, methods for nucleotide incorporation comprise: (a) providing a polymeric particle attached to a single-stranded oligonucleotide (e.g., a primer oligonucleotide); (b) providing a single-stranded template polynucleotide; (c) hybridizing the single-stranded oligonucleotide to the single-stranded template polynucleotide; and (d) contacting the single-stranded template polynucleotide with a polymerase and at least one nucleotide under conditions suitable for the polymerase to catalyze polymerization of at least one nucleotide onto the single-stranded oligonucleotide, thereby conducting nucleotide incorporation. In some embodiments, each of the polymeric particles can be attached with a plurality of single-stranded oligonucleotides (e.g., capture oligonucleotides). In some embodiments, steps (b), (c) or (d) can be conducted with a plurality of single-stranded polynucleotides. In some embodiments, at least a portion of the single-stranded oligonucleotide comprises a nucleotide sequence that is complementary (or partially complementary) to at least a portion of the single-stranded polynucleotide. In some embodiments, a system comprises a single-stranded polynucleotide hybridized to a single-stranded oligonucleotide which is attached to a polymeric particle, wherein at least one nucleotide is polymerized onto the end of the single-stranded oligonucleotide.

In another example, methods for primer extension can include: conducting a primer extension reaction on a polynucleotide that is hybridized to an oligonucleotide that is attached to a polymeric particle. In some embodiments, methods for nucleic acid primer extension comprise: (a) providing a polymeric particle attached to a single-stranded oligonucleotide (e.g., a primer oligonucleotide); (b) providing a single-stranded template polynucleotide; (c) hybridizing the single-stranded oligonucleotide to the single-stranded template polynucleotide; and (d) contacting the single-stranded template polynucleotide with a polymerase and at least one nucleotide under conditions suitable for the polymerase to catalyze polymerization of at least one nucleotide onto the single-stranded oligonucleotide, thereby extending the primer. In some embodiments, each of the polymeric particles can be attached with a plurality of single-stranded oligonucleotides (e.g., capture oligonucleotides). In some embodiments, step (b), (c) or (d) can be conducted with a plurality of single-stranded polynucleotides. In some embodiments, at least a portion of the single-stranded oligonucleotide comprises a nucleotide sequence that is complementary (or partially complementary) to at least a portion of the single-stranded polynucleotide. In some embodiments, a system comprises a single-stranded polynucleotide hybridized to a single-stranded oligonucleotide which is attached to a polymeric particle, wherein the single-stranded oligonucleotide is extended with one or more nucleotides.

In additional examples, methods for nucleic acid amplification comprise: conducting a primer extension reaction on a polynucleotide that is hybridized to an oligonucleotide which is attached to a polymeric particle. In some embodiments, methods for nucleic acid amplification comprise: (a) providing a polymeric particle attached to a single-stranded oligonucleotide (e.g., a primer oligonucleotide); (b) providing a single-stranded template polynucleotide; (c) hybridizing the single-stranded oligonucleotide to the single-stranded template polynucleotide; (d) contacting the single-stranded template polynucleotide with a polymerase and at least one nucleotide under conditions suitable for the polymerase to catalyze polymerization of at least one nucleotide onto the single-stranded oligonucleotide so as to generate an extended single-stranded oligonucleotide. In some embodiments, the method further comprises: (e) removing (e.g., denaturing) the single-stranded template polynucleotide from the extended single-stranded oligonucleotide so that the single-stranded oligonucleotide remains attached to the polymeric particle; (f) hybridizing the remaining single-stranded oligonucleotide to a second single-stranded template polynucleotide; and (g) contacting the second single-stranded template polynucleotide with a second polymerase and a second at least one nucleotide, under conditions suitable for the second polymerase to catalyze polymerization of the second at least one nucleotide onto the single-stranded oligonucleotide so as to generate a subsequent extended single-stranded oligonucleotide. In some embodiments, steps (e), (f) and (g) can be repeated at least once. In some embodiments, the polymerase and the second polymerase comprise a thermostable polymerase. In some embodiments, the conditions suitable for nucleotide polymerization include conducting the nucleotide polymerization steps (e.g., steps (d) or (g)) at an elevated temperature. In some embodiments, the conditions suitable for nucleotide polymerization include conducting the nucleotide polymerization step (e.g., steps (d) or (g)) at alternating temperatures (e.g., an elevated temperature and a relatively lower temperature). In some embodiments, the alternating temperature ranges from 60-95° C. In some embodiments, the temperature cycles can be about 10 seconds to about 5 minutes, or about 10 minutes, or about 15 minutes, or longer. In some embodiments, methods for nucleic acid amplification can generate one or more polymeric particles each attached to a plurality of template polynucleotides comprising sequences that are complementary to the single-stranded template polynucleotide or to the second single-stranded template polynucleotide. In some embodiments, each of the polymeric particles can be attached with a plurality of single-stranded oligonucleotides (e.g., capture oligonucleotides). In some embodiments, step (b), (c), (d), (e), (f) or (g) can be conducted with a plurality of single-stranded polynucleotides. In some embodiments, at least a portion of the single-stranded oligonucleotide comprises a nucleotide sequence that is complementary (or partially complementary) to at least a portion of the single-stranded polynucleotide. In some embodiments, methods for nucleic acid amplification (as described above) can be conducted in an aqueous phase solution in an oil phase (e.g., dispersed phase droplet).

Following PCR, particles are formed, such as particle 310, which can include the hydrophilic particle 312 and a plurality of copies 314 of the target polynucleotide or complements thereof. While the polynucleotides 314 are illustrated as being on a surface of the particle 310, the polynucleotides 314 can extend within the particle 310. Hydrogel and hydrophilic particles having a low concentration of polymer relative to water can include polynucleotide segments on the interior of and throughout the particle 310 or polynucleotides can reside in pores and other openings. In particular, the particle 310 can permit diffusion of enzymes, nucleotides, primers and reaction products used to monitor the reaction. A high number of polynucleotides per particle produces a better signal in particular sequencing techniques.

In an exemplary embodiment, the particle 310 can be utilized in a sequencing device. For example, a sequencing device 316 can include an array of wells 318. A particle 310 can be placed within a well 318.

In an example, a primer can be added to the wells 318 or the particle 310 can be pre-exposed to the primer prior to placement in the well 318. The primer and polynucleotide form a nucleic acid duplex including the polynucleotide (e.g., a template nucleic acid) hybridized to the primer. The nucleic acid duplex is an at least partially double-stranded polynucleotide. Enzymes and nucleotides can be provided to the well 318 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 316 and can migrate to the well 318. Excitation energy can be also provided to the well 318. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 318 can change. Such a change in pH can be detected by ion sensitive field effect transistors (ISFET). As such, a change in pH can be used to generate a signal indicating the order of nucleotides complementary to the polynucleotide 314 of the particle 310.

In particular, a sequencing system can include a well, or a plurality of wells, disposed over a sensor pad of an ionic sensor, such as a field effect transistor (FET). In some embodiments, a system includes one or more polymeric particles loaded into a well which is disposed over a sensor pad of an ionic sensor (e.g., FET), or one or more polymeric particles loaded into a plurality of wells which are disposed over sensor pads of ionic sensors (e.g., FET). In some embodiments, an FET can be a chemFET or an ISFET. A "chemFET" or chemical field-effect transistor, includes a type of field effect transistor that acts as a chemical sensor. It is the structural analog of a MOSFET transistor, where the charge on the gate electrode is applied by a chemical process. An "ISFET" or ion-sensitive field-effect transistor can be used for measuring ion concentrations in solution; when the ion concentration (such as H+) changes, the current through the transistor changes accordingly.

The FET may be a FET array. As used herein, an "array" is a planar arrangement of elements such as sensors or wells. The array may be one or two dimensional. A one dimensional array can be an array having one column (or row) of elements in the first dimension and a plurality of rows (or columns) in the second dimension. The number of columns (or rows) in the first and second dimensions may or may not be the same.

One or more microfluidic structures can be fabricated above the FET sensor array to provide for containment or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, or concentration in the given well. In some embodiments, there can be a 1:1 correspondence of FET sensors and reaction wells.

Returning to FIG. 3, in another example, a well 318 of the array of wells can be operatively connected to measuring devices. For example, for fluorescent emission methods, a well 318 can be operatively coupled to a light detection device. In the case of ionic detection, the lower surface of the well 318 may be disposed over a sensor pad of an ionic sensor, such as a field effect transistor.

One exemplary system involving sequencing via detection of ionic byproducts of nucleotide incorporation is the Ion Torrent PGM™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ sequencer detects the nucleotide incorporations by detecting the hydrogen ion byproducts of the nucleotide incorporations. The Ion Torrent PGM™ sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

EXAMPLE

Example 1

Figure 4:
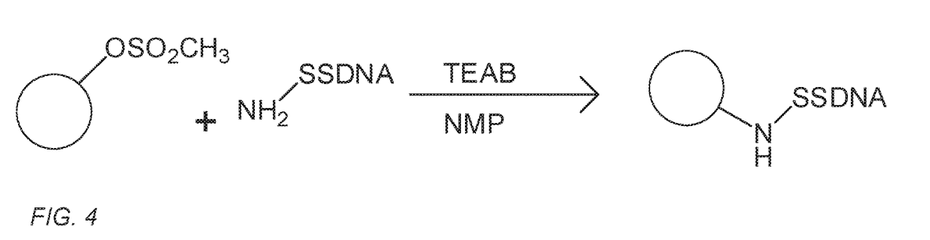
FIG. 4 includes an illustration of an exemplary direct conjugation method.

An oligonucleotide is directly conjugated to a mesyl activated Dynal particle, as illustrated in FIG. 4. While functional groups are illustrated as being on the surface of the particle, functional groups can exist throughout the particle. Mesyl chloride activated microgels are prepared via the Ugelstad process, a seeded emulsion polymerization. Thus formed particles are washed in N-methyl-2-pyrrolidone (NMP) in preparation for conjugation with ion exchanged single stranded DNA.

The sodium salt of 5'-NH2-C6-30-mer oligonucleotide was dissolved in 0.1 M tetrabutylammonium acetate, and injected onto a reverse phase HPLC column. Elution was performed with 0.1 M tetrabutylammonium acetate mobile phase. The fraction containing nucleic acid was collected, lyophilized to a dry powder, and re-suspended in dry N-methyl-2-pyrrolidone (NMP).

Five million particle ($5.0 \times 10^9$) are dispersed in 350 uL of anhydrous NMP and vortex mixed to disperse. 124 uL of Bu4NAc-DNA (5'-NH2-C6-30-mer oligonucleotide) in NMP (4.10 mM) is directly added to the particle mixture. 19.5 uL of tetraethylammonium borate (26.14 mM) is then added to the reaction mixture for a final volume of ~500 uL.

The reaction mixture is quickly vortex mixed and is gently mixed at 70° C. for 16 hours. The mixture is centrifuged, the supernatant is decanted, and the particles are re-suspended in 1 mL of NMP. After vortex mixing, the re-suspended microgel particles are pelleted with two cycles of precipitation/dispersion in NMP. After the second NMP wash, the pellets are brought up in 1 mL of 2×SSPE/0.1% sodium dodecyl sulfate (SDS), mixed and centrifuged to pellets. Finally, the particles are brought up in 1 mL of 1×PBS/0.1% Triton X-100, mixed and centrifuged to a firm pellet, repeating this process three times. After the final cycle, the conjugated microgels are re-suspended in 500 uL 1×PBS/0.1% Triton X-100.

The conjugated materials are then counted after labeling with SYBR-gold stain with a flow cytometer. The materials are ready for PCR amplification of DNA template in preparation for sequencing.

Example 2

Figure 5:
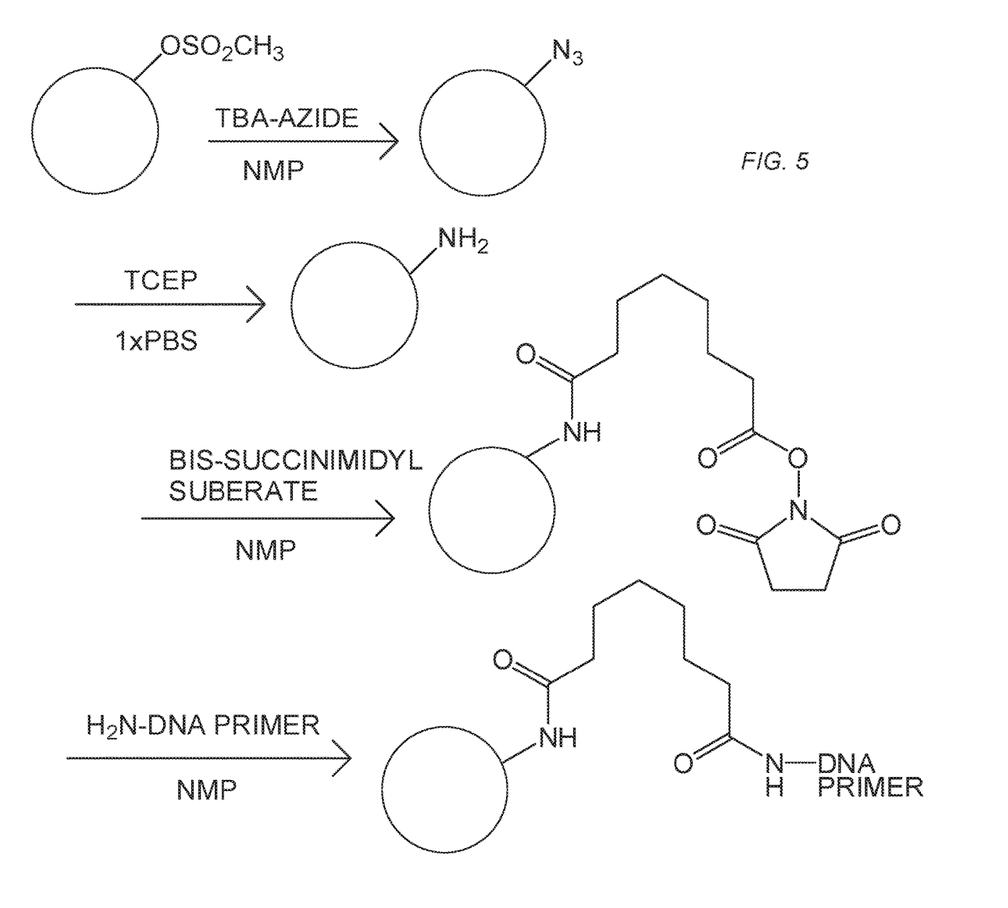
FIG. 5 includes an illustration of an exemplary indirect conjugation method.

A particle is conjugated through a series of substitutions as illustrated in FIG. 5. While functional groups are illustrated as being on the surface of the particle, functional groups can exist throughout the particle.

To a solution of mesyl chloride activated hydrogels in NMP (2 billion, 1 ml) in 2 ml centrifuge tube, a solution of saturated tetrabutylammonium azide in NMP (800 uL) is added, and the reaction mixture is stirred overnight at 60° C. The reaction mixture is centrifuged at 21300 rcf for 10 min and supernatant is removed. A resulting pellet is re-suspended in NMP and centrifuged to remove supernatant. The process is repeated two times.

A resulting pellet is re-suspended in de-ionized (DI) water (1 ml). The reaction mixture is centrifuged at 21300 rcf for 10 min and supernatant is removed. The process is repeated 2 more times.

To the pellet, 1 ml of TCEP solution (DI water, 1M) is added and the reaction mixture is stirred at room temperature overnight. The reaction mixture is centrifuged to remove supernatant at 21300 rcf for 10 min. The resulting pellet is re-suspended in DI water and is centrifuged at 21300 rcf for 10 min to remove supernatant two more times. The reaction mixture is re-suspended in anhydrous NMP (1 ml) and is centrifuged at 21300 rcf for 10 min. The supernatant is removed, and the process is repeated 3 more times.

The resulting pellet is re-suspended in anhydrous NMP (500 ul) and a solution of Bis-NHS suberate in anhydrous NMP (200 uL, 20 mg) is added to the reaction mixture. The reaction mixture is stirred at 70° C. overnight. The reaction mixture is centrifuged to remove supernatant at 21300 rcf for 10 min. The reaction mixture is re-suspended in anhydrous NMP (1 ml) and is centrifuged to remove supernatant at 21300 rcf for 10 min. The process is repeated five more times, and a resulting pellet is re-suspended in anhydrous NMP (200 uL).

To the reaction mixture, a solution of oligonucleotide (Bu4NAc-DNA (5'-NH2-C6-30-mer oligonucleotide) in NMP) (0.6 micromole, 200 uL) and a solution of tetrabutylammonium borate in anhydrous NMP (60 uL, 1 mg in 200 uL) is added, and the reaction mixture is stirred at 70° C. overnight.

The reaction mixture is centrifuged at 21300 rcf for 10 min to remove supernatant and a resulting pellet is re-suspended in NMP (1 ml). The reaction mixture is centrifuged at 21300 rcf for 10 min and the resulting pellet is re-suspended in NMP. The process is repeated three more times, and the pellet is re-suspended in 2×SSPE+0.2% SDS solution (1 ml) and is centrifuged at 21300 rcf for 10 min. The resulting pellet is re-suspended in 1×TE buffer with 0.1% Triton X100 (1 ml). The reaction mixture is centrifuged at 21300 rcf for 10 min. The pellet is re-suspended in 1×FE buffer and stirred at 80° C. for 1 h. The mixture is centrifuged at 21300 rcf for 10 min to remove the supernatant. The pellet is re-suspended in 1×FE buffer with 0.1% Triton X100 (1 ml) and is centrifuge at 21300 rcf for 10 min to remove the supernatant. The process is repeated once. The pellet is re-suspended in 30% ammonia solution (1 ml) and is stirred at room temperature for 15 min. The reaction mixture is centrifuged to remove the supernatant at 21300 rcf for 10 min, and the pellet is re-suspended in DI water (1 ml). The reaction mixture is centrifuged at 21300 rcf for 10 min to remove the supernatant, and the process is repeated two more times. The pellet is re-suspended in 1×TE buffer with 0.1% Triton X100 (1 ml). The reaction mixture is centrifuged at 21300 rcf for 10 min to remove the supernatant, and the process is repeated one more time. The pellet is re-suspended in 1×TE buffer with 0.1% Triton X100, and the reaction mixture is centrifuged at 21300 rcf for 10 min to remove the supernatant. The process is repeated one more time, and the pellet is re-suspended in 1×TE buffer with 0.1% Triton X100 (500 uL).

Example 3 Activation of an Amino-Hydrogel and Conjugation of the Hydrogel with Amine Terminal DNA Probe To a solution of 100 billion of amino-hydrogel (diameter=0.55 microns, 23 million amines/micron3) in anhydrous, amine-free N-methylpyrrolidone (NMP) (600 μL) is added solid bis-succinimidyl suberate (22.1 mg, 60 μmole), followed by tributylamine (14 μL, 60 μmole). After stirring at 60 C for 1 h the hydrogels are isolated by centrifugation (30 min at 21300 rcf). The hydrogel pellet is diluted with amine-free anhydrous NMP (1 ml) and isolated by centrifugation; this washing process is repeated 2 times, and the final pellet is re-suspended in NMP (600 μL). This hydrogel suspension is treated with acetic anhydride (30 μL, 317 μmole) and tributylamine (30 μL, 126 μmole), and is stirred at room temperature for 2 h. The resulting hydrogel is isolated by centrifugation (30 min at 21300 rcf) and the pellet is diluted with amine-free anhydrous NMP (1 ml) and isolated by centrifugation; this washing process is repeated 2 times, and the final activated, capped pellet is diluted with 1☐μmole of a 3 μmolar NMP solution of tetrabutylammonium 5'-amino-oligonucleotide, tributylamine (1☐μmole), and amine-free NMP to a final volume of 600 μL. After stirring at 70 C for 16 h, the DNA conjugated hydrogel is isolated by centrifugation (30 min at 21300 rcf). The pellet is washed with NMP (1 ml), followed by Deionized water wash (1 ml) using centrifugation to isolate the pellets. The final hydrogel pellet is diluted with 1×TE buffer (1.6 ml) and stirred at 80 C for 1 h. The hydrogels are isolated by centrifugation (30 min at 21300 rcf) and washed twice with DI water (1 ml) (using centrifugation for pellet isolation). To the final pellet is added 30% aqueous ammonia; after 15 minutes at room temperature, the hydrogel is isolated centrifugation (20 min at 21300 rcf) and washed 3× with DI water (1 mL) using centrifugation for isolation. The final pellet is re-dispersed in the buffer desired for performing target amplification.

Example 4

Figure 6:
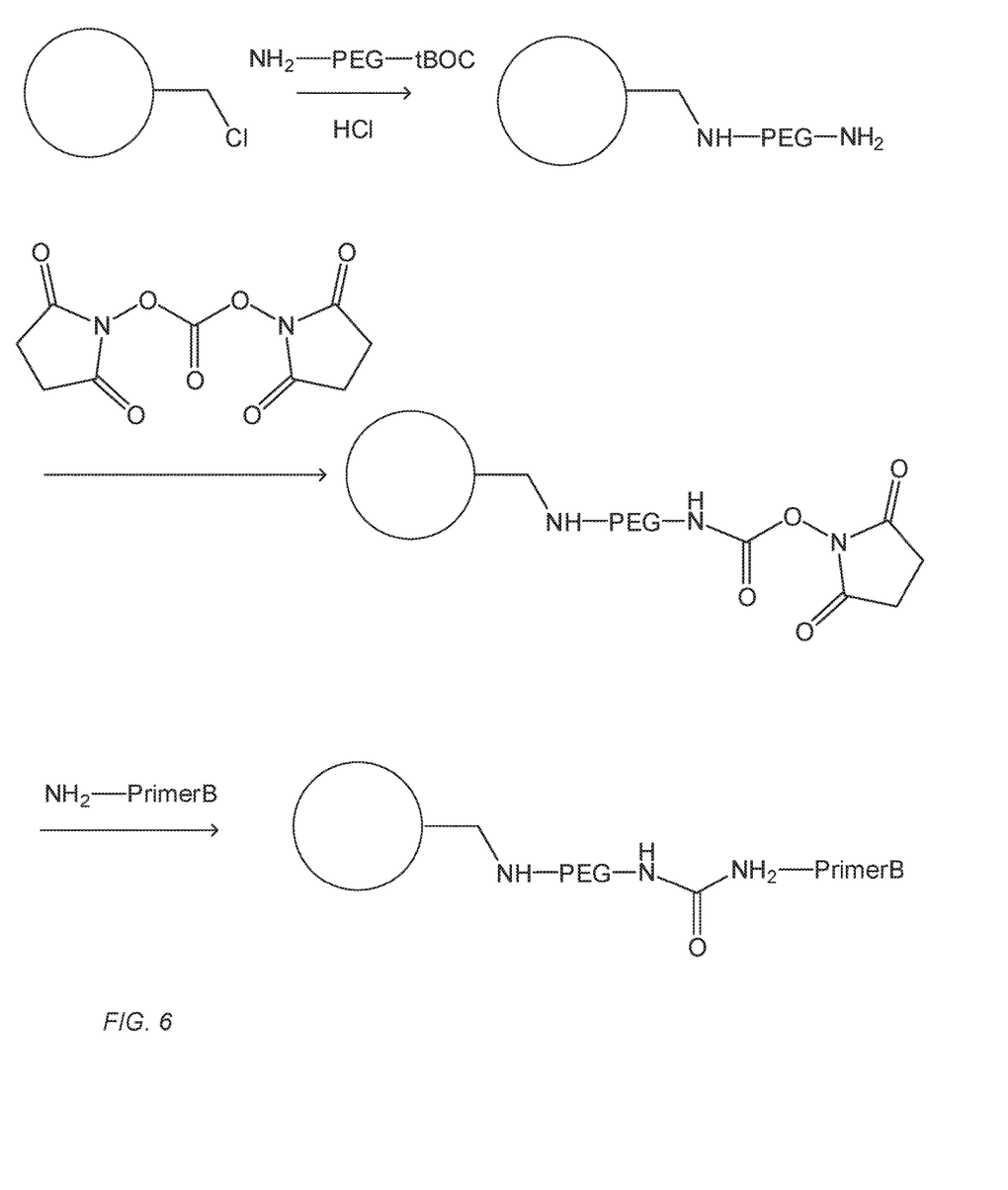
FIG. 6 includes an illustration of an exemplary conjugation method.

Functionalization of a mesylated hydrogel with a mono-protected diamine with subsequent deprotection, activation, and conjugation with an organic soluble DNA probe is illustrated in FIG. 6.

To a pellet of 200 billion of mesylatedhydrogel (diameter=0.6 microns) (concentrated by centrifugation in anhydrous, amine-free N-methylpyrrolidone (NMP)) is added 1 mL of mono-t-Boc protected diamine: O-(2-Aminoethyl)-O'-[2-(Boc-amino)ethyl]hexaethylene glycol as a as a 50 mM solution. After agitation for 12 hr at 70 C, the hydrogel is isolated by centrifugation, washed once with de-ionized water, and de-protected at room temperature in 1 mL of 30% aqueous HCl; after 1 hr, the hydrogel is isolated by centrifugation, and washed 5 times with 5 mL portions de-ionized water. The hydrogel is dehydrated by centrifugation of the aqueous suspension, and dilution with 1 mL of anhydrous, amine free NMP; this process is repeated 3 more times. After the final centrifugation, the pellet is activated with 0.6 mL of 125 mM of an NMP solution of disuccinimidyl carbonate, to which was added 30 μL of tributylamine; after 2 hr at room temperature, the activated hydrogel is isolated by centrifugation, and the pellet is washed 5 times with 1 mL portions of anhydrous, amine free NMP. To the resulting pellet is added 0.5 mL of a 3 μmolar NMP solution of tetrabutylammonium 5'-amino-oligonucleotide and tributylamine (30 μL); after agitation for 12 hr at 70° C., the conjugated hydrogel is concentrated by centrifugation and washed 3 time with 1 mL portions of NMP. The conjugated hydrogel pellet is diluted with 1×TE buffer (1.6 ml) and stirred at 80 C for 1 hr and subsequently isolated by centrifugation. After washing twice with de-ionized water, the final pellet was re-dispersed in the buffer desired for performing target amplification.

In a first aspect, a method of conjugating a substrate includes exchanging a counter ion associated with a biomolecule with a lipophilic counter ion to form a biomolecule complex, dispersing the biomolecule complex in a nonaqueous solvent, and coupling the biomolecule complex to a substrate in the presence of the nonaqueous solvent.

In an example of the first aspect, the biomolecule is a polynucleotide.

In another example of the first aspect and the above example, the lipophilic counter ion is a lipophilic ammonium ion, a lipophilic phosphonium ion, a lipophilic arsonium ion, a lipophilic sulfonium ion, or a combination thereof. For example, the lipophilic ammonium ion is a tetraalkylammonium, a tetraarylammonium, mixed alkyl and aryl ammonium, or a combination thereof. In an example, the lipophilic ammonium ion is selected from the group consisting of tetramethylamonium, tetraethylamonium, tetrapropylamonium, tetrabutylamonium, tetrapentylamonium, tetrahexylamonium, tetraheptylamonium, tetraoctylamonium, alkyl and aryl mixtures thereof, and a combination thereof. In a further example, the lipophilic phosphonium ion is tetraphenylphosphonium. In an additional example, the lipophilic arsonium ion is a tetraalkylarsonium, a tetraarylarsonium, a mixed alkyl and aryl arsonium ion, or a combination thereof. In another example, the lipophilic arsonium ion is tetraphenylarsonium. In an example, the lipophilic sulfonium ion is a trialkylsulfonium ion.

In a further example of the first aspect and the above examples, the nonaqueous solvent is non-reactive with coupling groups on the substrate and the biomolecule.

In an additional example of the first aspect and the above examples, the nonaqueous solvent is polar.

In another example of the first aspect and the above examples, the nonaqueous solvent is an amide, a urea, a carbonate, an ether, a sulfoxide, a sulfone, a hindered alcohol, or a combination thereof. For example, the amide or urea is selected from a group consisting of formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, and a combination thereof. In another example, the carbonate is selected from a group consisting of dimethyl carbonate, propylene carbonate, and a combination thereof. In an additional example, the ether is tetrahydrofuran. In a further example, the sulfoxide or sulfone is selected from a group consisting of dimethylsulfoxide, dimethylsulfone, and a combination thereof. In another example, the hindered alcohol includes tert-butyl alcohol.

In a further example of the first aspect and the above examples, the substrate includes a polymeric particle.

In an additional example of the first aspect and the above examples, the polymeric particle includes a coupling group reactive with a reactive group of the biomolecule.

In an example of the first aspect and the above examples, the coupling group includes one of a nucleophile or an electrophile and the reactive group includes the other of the nucleophile or the electrophile.

In a second aspect, a method of conjugating a polymeric particle includes exchanging a cationic counter ion associated with a polynucleotide with a lipophilic cationic counter ion to form a polynucleotide complex, the polynucleotide including a nucleophilic or an electrophilic reactive group. The method further includes dispersing the polynucleotide complex in a non-reactive, nonaqueous solvent and coupling the polynucleotide to the polymeric particle by nucleophilic or electrophilic substitution, the polymeric particle including an electrophilic group or a nucleophilic group.

In a third aspect, a polymeric particle includes a polymer conjugated to a polynucleotide using the method of any one of above aspects or examples.

In a fourth aspect, a method of sequencing includes amplifying a target polynucleotide in the presence of an oligonucleotide conjugated polymeric particle to form the polynucleotide conjugated polymeric particle. The oligonucleotide is at least partially complementary to the target polynucleotide. The oligonucleotide conjugated polymeric particle is formed by the method of any of the above aspects or examples. The method further includes applying the polynucleotide conjugated polymeric particle to a sequencing device, applying a primer to the polynucleotide conjugated polymeric particle, incorporating a nucleotide, and detecting the incorporating.

In an example of the fourth aspect, detecting includes detecting a change in ion concentration associated with incorporation of a nucleotide.

In a fifth aspect, a method of isolating a target polynucleotide includes contacting a first solution including the target polynucleotide with a probe conjugated substrate. The probe of the probe conjugated substrate is at least partially complementary to the target polynucleotide. The probe conjugated substrate formed by the method of any of the above aspects or examples. The method further includes washing the probe conjugated substrate while the target polynucleotide is coupled to the probe and releasing the target polynucleotide in a second solution.

In an additional aspect, a method of conjugating an oligonucleotide to a polymer includes treating a polymer comprising amine functionality with a bis-NHS ester or a disuccinimidyl carbonate to form a functionalized polymer and treating the functionalized polymer with an amine terminated oligonucleotide to form a conjugated polymer including the oligonucleotide.

In an example of the additional aspect, the method further includes providing an initial polymer including hydroxyl functionality, treating the initial polymer to substitute a halogen for the hydroxyl functionality, and further treating the initial polymer with a protected amine terminated polyether to form the polymer comprising the amine functionality.

In another example of the additional aspect and the above example, the polymer is in the form of a polymer particle.

In a further example the oligonucleotide undergoes a treatment of the methods of the above aspects and examples thereof.

While the above describes conjugation to polymer particles, such conjugation methods can be applied to similarly functionalized polymer in various forms, such as beads, substrates, sheets, rods, variously shaped polymer forms, or any combination thereof.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of conjugating an oligonucleotide to a polymer, the method comprising:
   treating a polymer comprising amine functionality with a bis-NHS ester or a disuccinimidyl carbonate to form a functionalized polymer to form a substrate having coupling groups; and
   treating the functionalized polymer with an amine terminated oligonucleotide to form a conjugated polymer including the oligonucleotide in the presence of a nonaqueous solvent, wherein the nonaqueous solvent is non-reactive with the coupling groups on the substrate and the amine terminated oligonucleotide.

2. The method of claim 1, further comprising:
   providing an initial polymer including hydroxyl functionality;
   treating the initial polymer to substitute a halogen for the hydroxyl functionality; and
   further treating the initial polymer with a protected amine terminated polyether to form the polymer comprising the amine functionality.

3. The method of claim 1, wherein the polymer is in the form of a polymer particle.

4. The method of claim 1, further comprising:
   exchanging a counter ion associated with the amine terminated oligonucleotide with a lipophilic counter ion prior to treating the functionalized polymer;
   dispersing the amine terminated oligonucleotide in the nonaqueous solvent; and
   coupling the amine terminated oligonucleotide to the substrate in the presence of the nonaqueous solvent.

5. The method of claim 4, wherein the lipophilic counter ion is a lipophilic ammonium ion, a lipophilic phosphonium ion, a lipophilic arsonium ion, a lipophilic sulfonium ion, or a combination thereof.

6. The method of claim 5, wherein the lipophilic ammonium ion is a tetraalkylammonium, a tetraarylammonium, mixed alkyl and aryl ammonium, or a combination thereof.

7. The method of claim 6, wherein the lipophilic ammonium ion is selected from the group consisting of tetramethylamonium, tetraethylamonium, tetrapropylamonium, tetrabutylamonium, tetrapentylamonium, tetrahexylamonium, tetraheptylamonium, tetraoctylamonium, alkyl and aryl mixtures thereof, and a combination thereof.

8. The method of claim 5, wherein the lipophilic phosphonium ion is tetraphenylphosphonium.

9. The method of claim 5, wherein the lipophilic arsonium ion is a tetraalkylarsonium, a tetraarylarsonium, a mixed alkyl and aryl arsonium ion, or a combination thereof.

10. The method of claim 9, wherein the lipophilic arsonium ion is tetraphenylarsonium.

11. The method of claim 5, wherein the lipophilic sulfonium ion is a trialkylsulfonium ion.

12. The method of claim 1, wherein the nonaqueous solvent is polar.

13. The method of claim 1, wherein the nonaqueous solvent is an amide, a urea, a carbonate, an ether, a sulfoxide, a sulfone, a hindered alcohol, or a combination thereof.

14. The method of claim 13, wherein the amide or urea is selected from a group consisting of formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, and a combination thereof.

15. The method of claim 13, wherein the carbonate is selected from a group consisting of dimethyl carbonate, propylene carbonate, and a combination thereof.

16. The method of claim 13, wherein the ether is tetrahydrofuran.

17. The method of claim 13, wherein the sulfoxide or sulfone is selected from a group consisting of dimethylsulfoxide, dimethylsulfone, and a combination thereof.

* * * * *

UNITED STATES PATENT AND TRADEMARK OFFICE
CERTIFICATE OF CORRECTION

PATENT NO.        : 10,724,094 B2
APPLICATION NO.   : 15/945348
DATED             : July 28, 2020
INVENTOR(S)       : Menchen et al.

Page 1 of 1

It is certified that error appears in the above-identified patent and that said Letters Patent is hereby corrected as shown below:

In the Claims

Column 20, Lines 52-56, Please replace Claim 7 with the following:
-- The method of claim 6, wherein the lipophilic ammonium ion is selected from the group consisting of tetramethylammonium, tetraethylammonium, tetrapropylammonium, tetrabutylammonium, tetrapentylammonium, tetrahexylammonium, tetraheptylammonium, tetraoctylammonium, alkyl and aryl mixtures thereof, and a combination thereof. --

Signed and Sealed this
Eighth Day of December, 2020

Andrei Iancu
*Director of the United States Patent and Trademark Office*